US007813804B1

(12) United States Patent
Jaax

(10) Patent No.: US 7,813,804 B1
(45) Date of Patent: Oct. 12, 2010

(54) METHODS AND SYSTEMS FOR TREATING A NERVE COMPRESSION SYNDROME

(75) Inventor: Kristen N. Jaax, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 502 days.

(21) Appl. No.: 11/864,465

(22) Filed: Sep. 28, 2007

(51) Int. Cl.
A61N 1/36 (2006.01)
(52) U.S. Cl. ........................................................ 607/46
(58) Field of Classification Search .................... 607/46, 607/118, 117
See application file for complete search history.

(56) References Cited

U.S. PATENT DOCUMENTS 3,881,495 A * 5/1975 Pannozzo et al. ............. 607/55
5,387,231 A * 2/1995 Sporer ........................... 607/48
6,535,767 B1 * 3/2003 Kronberg ...................... 607/72
6,675,046 B2 1/2004 Holsheimer
6,733,485 B1 * 5/2004 Whitehurst et al. ......... 604/500
6,850,802 B2 2/2005 Holsheimer
6,892,097 B2 5/2005 Holsheimer
7,117,034 B2 * 10/2006 Kronberg ........................ 607/2
7,203,548 B2 * 4/2007 Whitehurst et al. ........... 607/39
2004/0015205 A1 1/2004 Whitehurst et al.

* cited by examiner

Primary Examiner—Carl H Layno
Assistant Examiner—Brian T Gedeon
(74) Attorney, Agent, or Firm—Frommer Lawrence & Haug LLP; Bruce E. Black

(57) ABSTRACT

Methods of treating a nerve compression syndrome include applying at least one stimulus to a stimulation site within a patient with an implanted stimulator in accordance with one or more stimulation parameters. The at least one stimulus is configured to treat the nerve compression syndrome.

20 Claims, 10 Drawing Sheets

METHODS AND SYSTEMS FOR TREATING A NERVE COMPRESSION SYNDROME

BACKGROUND

Neuropathic pain is the result of a malfunction somewhere in the nervous system. The site of the nervous system injury or malfunction can be either in the peripheral or central nervous system. Neuropathic pain is often triggered by disease or injury and is frequently described as having a burning, lancinating, or electric shock characteristic. Persistent allodynia—pain resulting from a non-painful stimulus, such as light touch—is also a common characteristic of neuropathic pain. Neuropathic pain is frequently chronic.

Chronic neuropathic pain is often caused by one or more nerves being compressed or entrapped. Nerve compression may result from direct external pressure or contusion related to trauma, work, hobbies, or sports activities. Additionally or alternatively, nerve compression may be caused by structural abnormalities within the body. The exact mechanism of nerve compression is not completely understood and may include varying degrees of friction and ischemia.

Clinical manifestations of nerve compression include pain, which may be sharp or burning, and paresthesia. In more severe cases, there may be weakness distal to the site of compression. Physical symptoms of nerve compression include muscle atrophy, weakness, and involuntary twitching of muscle fibers. A person's reflexes may also be affected, depending on the site of the compression. Pain associated with nerve compression is often intensified during sleep.

Nerve compression syndromes can affect many different parts of the body. For example, commonly affected locations in the upper extremity include the thoracic outlet, shoulder girdle, elbow, forearm, wrist, and thumb. Lower extremity nerve compression syndromes commonly occur in the pelvis and around the knee, ankle, and foot.

One of the more common nerve compression syndromes is carpal tunnel syndrome (CTS), which affects millions of Americans and results in billions of dollars of workers compensation claims every year. In CTS, the median nerve is compressed at the wrist and often results in tingling, numbness, sleep disruption, coldness, weakness, and/or pain. Most cases of CTS are idiopathic. While repetitive activities are often blamed for the development of CTS, the correlation is often unclear. Physiology and family history may also play a role in an individual's susceptibility to CTS.

Various treatment therapies have been used to treat or curtail the occurrence of CTS and other nerve compression syndromes. For example, immobilizing braces, massages, ultrasonic therapy, localized steroid injections, and anti-inflammatory drugs such as ibuprofen or aspirin have all been used with varying levels of success. Severe cases of nerve compression can sometimes be remedied through surgical procedures. For example, CTS may be alleviated through a surgical procedure in which the transverse carpal ligament is cut to relieve pressure from the compressed median nerve. However, each of these treatment therapies can be ineffective, offer only temporary relief, or cause other undesirable side effects.

SUMMARY

Methods of treating a nerve compression syndrome include applying at least one stimulus to a stimulation site within a patient with an implanted stimulator in accordance with one or more stimulation parameters. The at least one stimulus is configured to treat the nerve compression syndrome.

Systems for treating a nerve compression syndrome include a stimulator configured to be implanted at least partially within a patient and to generate at least one stimulus in accordance with one or more stimulation parameters adjusted to treat the nerve compression syndrome, a programmable memory unit in communication with the stimulator and programmed to store the one or more stimulation parameters to at least partially define the stimulus such that the stimulus is configured to treat the nerve compression syndrome, and means, operably connected to the stimulator, for applying the stimulus to a stimulation site within the patient.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for treating one or more nerve compression syndromes are described herein. An implanted stimulator is configured to apply at least one stimulus to a stimulation site within a patient in accordance with one or more stimulation parameters. The stimulus is configured to treat a nerve compression syndrome and may include electrical stimulation, drug stimulation, gene infusion, chemical stimulation, thermal stimulation, electromagnetic stimulation, mechanical stimulation, and/or any other suitable stimulation. As used herein, and in the appended claims, "treating" a nerve compression syndrome refers to any amelioration of one or more causes and/or one or more symptoms of the nerve compression syndrome. For example, the stimulation applied by the stimulator may be configured to mask pain associated with a nerve compression syndrome, regenerate damaged nerves within a compressed nerve region, alleviate pressure within the compressed nerve region, and/or treat the nerve compression syndrome in any other manner.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
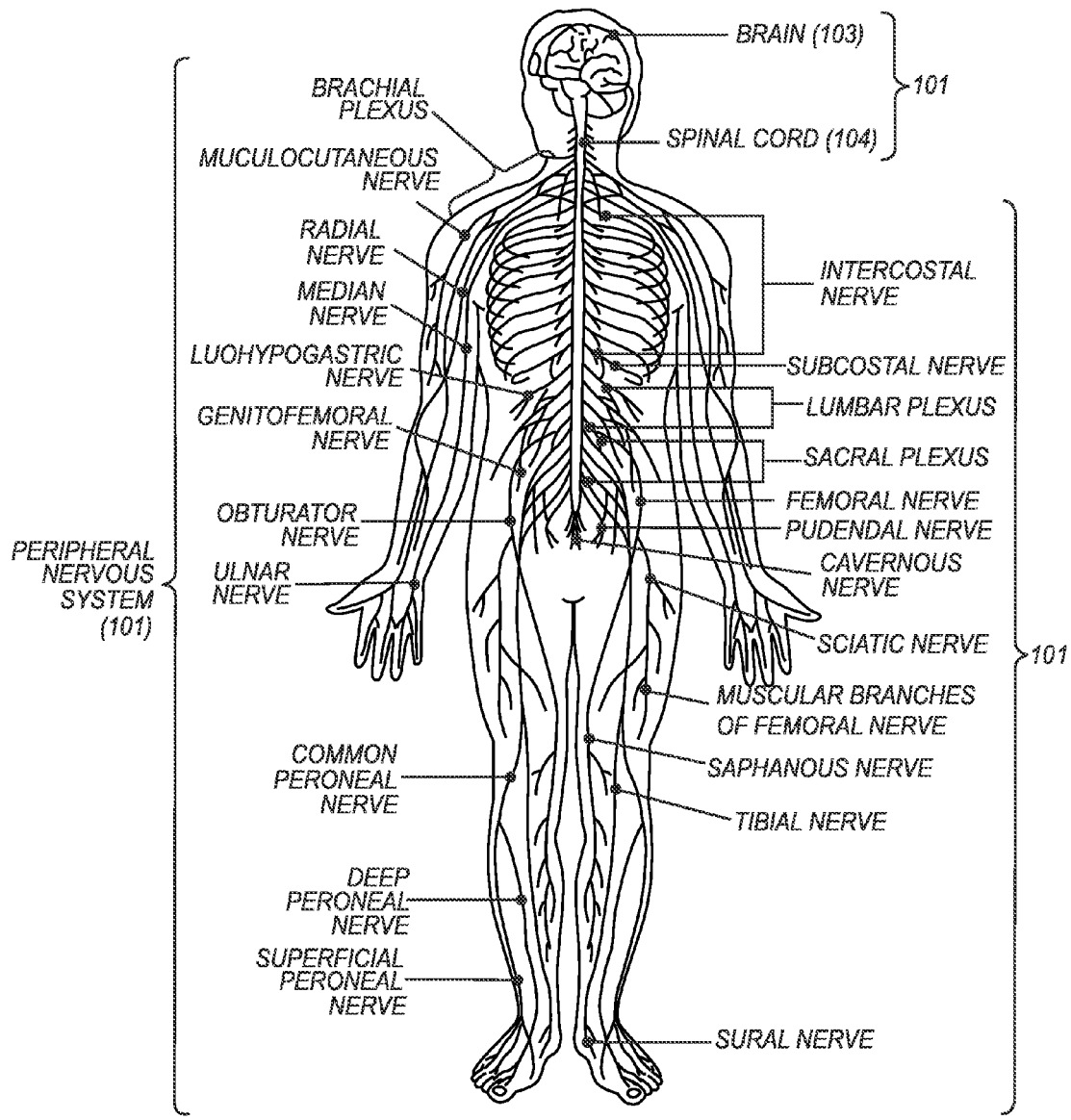
FIG. 1 is a diagram of the human nervous system.

Nerve compression syndromes affect many different nerves throughout the body. Hence, before discussing the present methods and systems for treating one or more nerve compression syndromes, a brief overview of the human nervous system will be given. FIG. 1A is a diagram of the human nervous system. The nervous system is divided into a central nervous system 100 and a peripheral nervous system 101. The central nervous system 100 includes the brain 102 and the spinal cord 103. The peripheral nervous system 101 includes a number of nerves that branch from various regions of the spinal cord 103. For example, the peripheral nervous system 101 includes, but is not limited to, the brachial plexus, the musculocutaneous nerve, the radial nerve, the median nerve, the iliohypogastric nerve, the genitofemoral nerve, the obturator nerve, the ulnar nerve, the peroneal nerve, the sural nerve, the tibial nerve, the saphenous nerve, the femoral nerve, the sciatic nerve, the cavernous nerve, the pudendal nerve, the sacral plexus, the lumbar plexus, the subcostal nerve, and the intercostal nerves.

The peripheral nervous system 101 may be further divided into the somatic nervous system and the autonomic nervous system. The somatic nervous system is the part of the peripheral nervous system 101 associated with the voluntary control of body movements through the action of skeletal muscles. The somatic nervous system consists of afferent fibers which receive information from external sources, and efferent fibers which are responsible for muscle contraction. The autonomic nervous system, on the other hand, regulates the involuntary action of various organs.

Figure 1B:
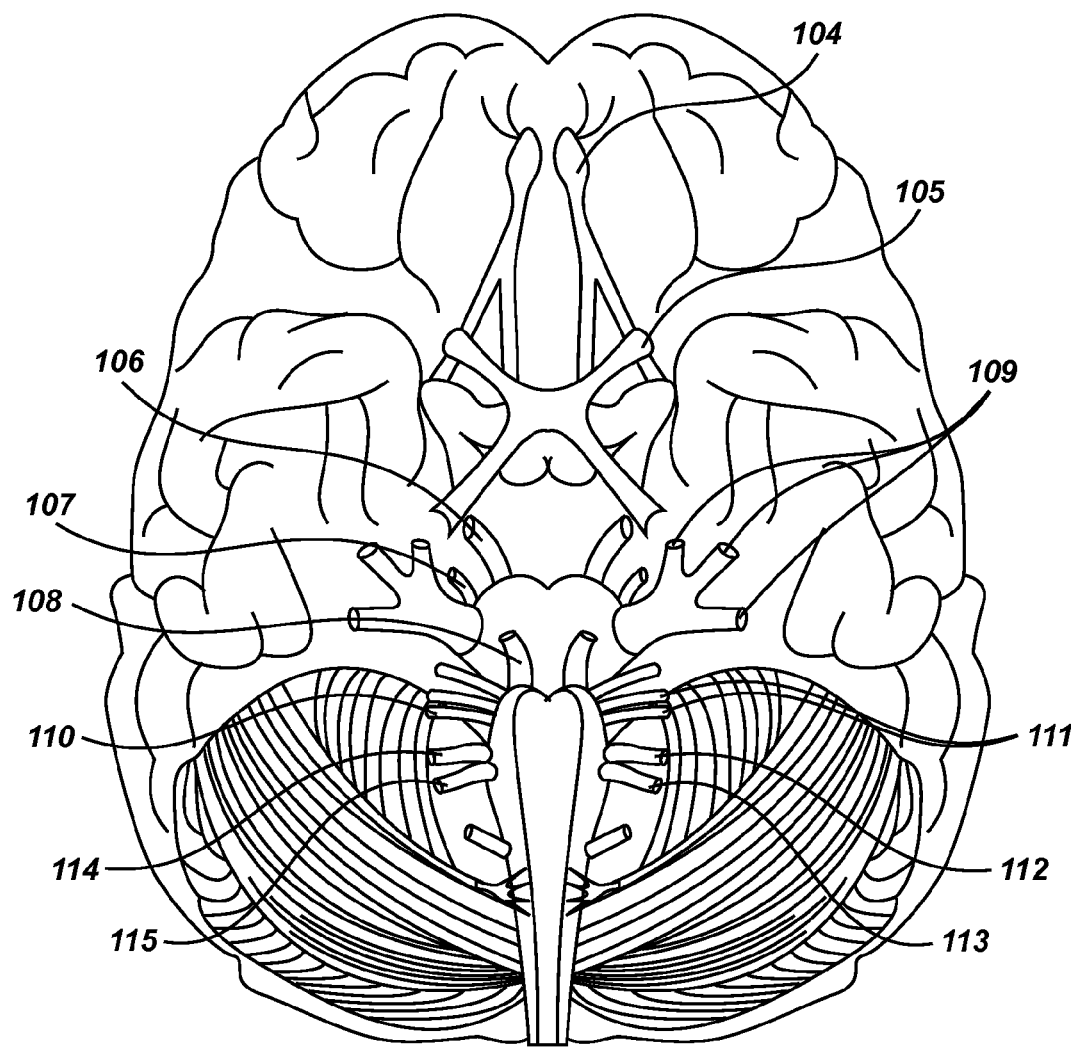
FIG. 1B is a perspective bottom view of the brain and illustrates a number of cranial nerves.

The peripheral nervous system also includes a number of cranial nerves that emerge from the brainstem. FIG. 1B is a perspective bottom view of the brain and illustrates a number of cranial nerves. The cranial nerves include twelve pairs of nerves that emanate from the brainstem: the olfactory nerve 104, optic nerve 105, oculomotor nerve 106, trochlear nerve 107, abducent nerve 108, trigeminal nerve 109, facial nerve 110, auditory nerve 111, glossopharyngeal nerve 112, vagus nerve 113, hypoglossal nerve 114, and accessory nerve 115. The oculomotor nerve 106, trochlear nerve 107, abducent nerve 108, trigeminal nerve 109, facial nerve 110, auditory nerve 111, glossopharyngeal nerve 112, vagus nerve 113, hypoglossal nerve 114, and accessory nerve 115 are all a part of the peripheral nervous system. The olfactory nerve 104 and optic nerve 105 are continuations of the central nervous system.

The cranial nerves control various muscles, organs, and other tissue throughout the body. For example, the oculomotor, trochlear, and abducent nerves control movement and function of the eye. The trigeminal nerve gives sensations to the face. The facial nerve controls facial expression and taste for two-thirds of the tongue. The hypoglossal nerve controls most of the tongue muscles as well as various other muscles. The accessory nerve controls muscles of the neck. The other cranial nerves are responsible for innervating other portions of the body.

As mentioned, when one or more of the nerves mentioned above become compressed or entrapped, a patient may experience one or more nerve compression syndromes. A number of nerve compression syndromes that may be treated by the systems and methods described herein will now be described for illustrative purposes. However, it will be recognized that the systems and methods described herein may additionally or alternatively be used to treat any type of nerve compression syndrome not specifically described herein.

One of the most common nerve compression syndromes is carpal tunnel syndrome. In carpal tunnel syndrome, the median nerve is compressed, resulting in tingling, numbness, sleep disruption, coldness, weakness, and/or pain. Pain is often felt in the thumb, first two fingers, and the medial half of the ring finger. Paresthesia and sensory deficits may involve the entire palm area in some cases due to variable nerve innervation. In addition, pain may radiate proximally to the forearm and, in extreme cases, to the shoulder.

Other nerve compression syndromes that affect the arm, wrist, and hand include, but are not limited to, cubital tunnel syndrome, radial tunnel syndrome, pronator syndrome, high radial nerve palsy, and lateral antebrachial cutaneous nerve entrapment syndrome.

Nerve compression syndromes also affect various locations within the leg. For example, meralgia paresthetica is a common nerve compression disorder that affects the thigh. In meralgia paresthetica, the lateral femoral cutaneous nerve typically becomes entrapped and unduly stimulated at some point in its course by muscle, tendon, ligament, or bone. The entrapped nerve results in pain and/or dysfunctional, disturbing sensations in the lateral aspect of the thigh on the affected side.

In tarsal tunnel syndrome, a painful nerve compression syndrome that affects the foot, the tibial nerve is impinged and compressed as it travels though the tarsal tunnel, which is found along the inner leg behind the medial malleolus. Tarsal tunnel syndrome is also known as posterior tibial nerve neuralgia and causes numbness, tingling, and pain in the first three toes and, in severe cases, in other locations of the foot and ankle.

Other nerve compression syndromes that affect the leg may be caused by compression of the peroneal nerve as it courses over the head of the fibula. Entrapment of the peroneal nerve may be the result of excessive crossing of legs, diabetes mellitus, marked weight loss, and local metastatic disease. Symptoms of a compressed peroneal nerve include, but are not limited to, peripheral motor weakness involving the ipsilateral foot.

Nerve compression syndromes also affect various nerves in the brachial plexus and shoulder areas. For example, a nerve compression syndrome called thoracic outlet syndrome is caused by obstruction of the neurovascular bundle serving the arm as the bundle passes from the thoracocervical region within the body to the axilla. Compression of the long thoracic nerve can produce paralysis and winging of the scapula. Suprascapular nerve impingement can also produce paralysis and pain within the shoulder. The triangular space between the scalene muscles, the costoclavicular space, and the pectoralis minor muscle are frequent sites for congenital and acquired lesions that can lead to obstruction of the neurovascular bundle serving the arm.

Nerve compression syndromes also affect the pelvic region and may be caused by compression or entrapment of the obturator nerve or the lateral femoral cutaneous nerve. Obturator nerve compression often results in pain in the groin and paresthesia that travels down the inner aspect of the thigh. Nerve compression syndromes in the pelvic region may develop following a pelvic fracture, osteitis pubis, an obturator hernia, or any other medical condition affecting the pelvic region.

Nerve compression syndromes may also be caused by compression of one or more of the cranial nerves. For example, trigeminal neuralgia is a nerve compression syndrome that affects the trigeminal nerve and causes episodes of intense pain in the eyes, lips, nose, scalp, forehead, and jaw. Trigeminal neuralgia can be caused by damage to the myelin sheath of the trigeminal nerve, an aneurysm, a tumor, an arachnoid cyst in the cerebellopontine angle, or a traumatic event such as a car accident.

It is believed that applying a stimulus to one or more nerves associated with one or more nerve compression syndromes may be useful in treating one or more nerve compression syndromes. As mentioned, "treating" a nerve compression syndrome refers to any amelioration or prevention of one or more causes, symptoms, and/or sequelae of the nerve compression syndrome.

Consequently, a stimulator may be implanted within a patient to deliver a stimulus to one or more stimulation sites within the patient to treat one or more nerve compression syndromes. The stimulus may include an electrical stimulation current, one or more drugs or other chemical stimulation, thermal stimulation, electromagnetic stimulation, mechanical stimulation, and/or any other suitable stimulation.

The one or more stimulation sites referred to herein, and in the appended claims, may include, but are not limited to, any nerve associated with any nerve compression syndrome. For example, the one or more stimulation sites may include, but are not limited to, one or more of the nerves associated with one or more of the nerve compression syndromes described herein such as, but not limited to, the median nerve, the ulnar nerve, the radial nerve, the lateral femoral cutaneous nerve, the suprascapular nerve, the long thoracic nerve, the axillary nerve, the posterior interosseous nerve, the anterior interosseous nerve, the lateral antebrachial cutaneous nerve, the brachial plexus, the obturator nerve, the peroneal nerve, the sciatic nerve, one or more of the cranial nerves, and/or the tibial nerve.

As used herein, and in the appended claims, the term "stimulator" will be used broadly to refer to any device that delivers a stimulus, such as an electrical stimulation current, one or more drugs or other chemical stimulation, thermal stimulation, electromagnetic stimulation, mechanical stimulation, and/or any other suitable stimulation at a stimulation site to treat one or more nerve compression syndromes. Thus, the term "stimulator" includes, but is not limited to, a microstimulator, implantable pulse generator (IPG), spinal cord stimulator (SCS), system control unit, deep brain stimulator, drug pump, or similar device.

Figure 2:
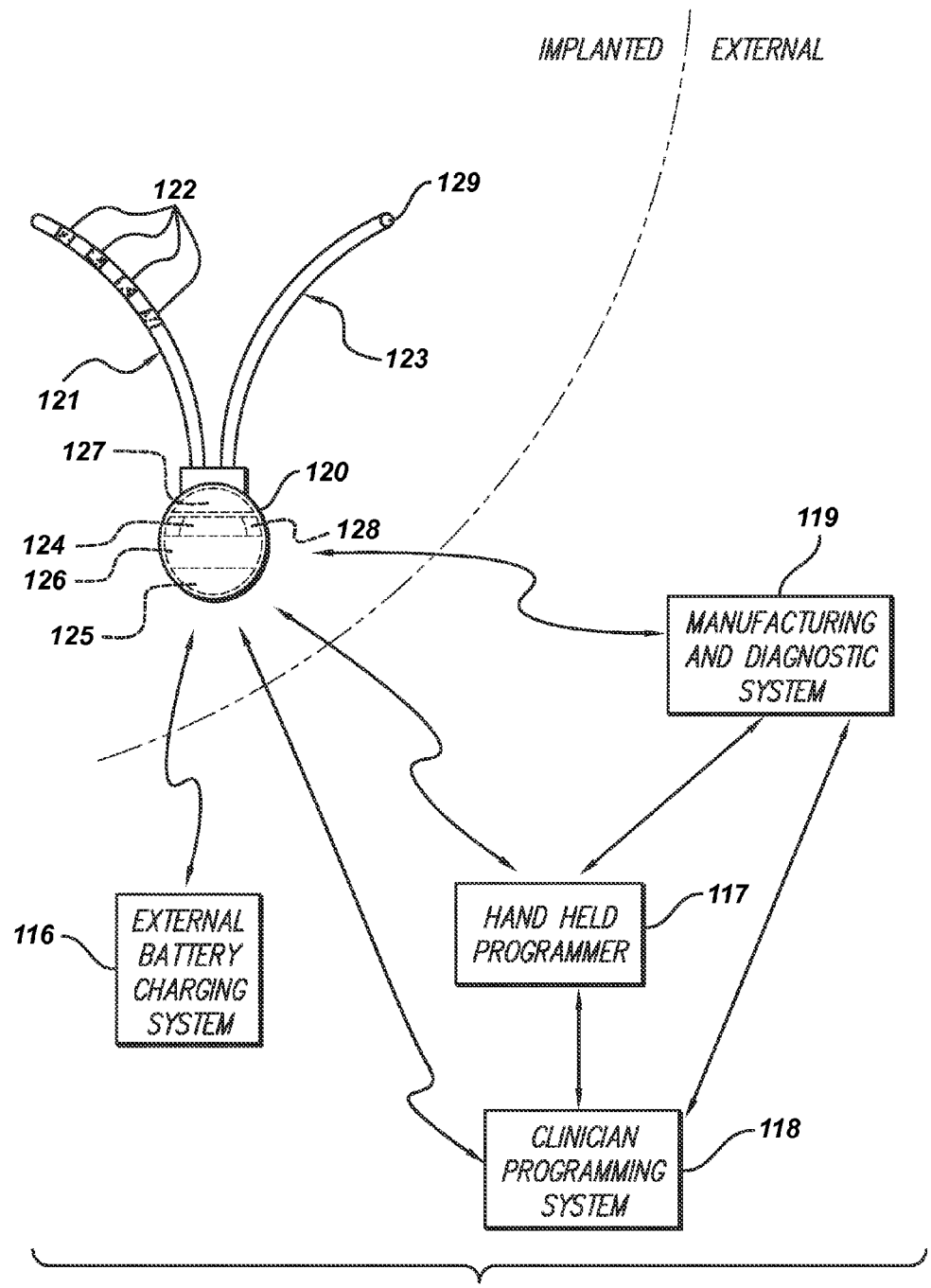
FIG. 2 illustrates an exemplary stimulator that may be used to apply a stimulus to a stimulation site within a patient to treat one or more nerve compression disorders according to principles described herein.

To facilitate an understanding of the methods of treating one or more nerve compression syndromes with an implanted stimulator, a more detailed description of an exemplary stimulator and its operation will now be given with reference to the figures. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied to a stimulation site. It will be recognized that the at least one lead 121 may include any number of electrodes 122 arranged in any configuration as best serves a particular application. In some alternative examples, as will be described in more detail below, the stimulator 120 is leadless.

As illustrated in FIG. 2, the stimulator 120 includes a number of components. It will be recognized that the stimulator 120 may include additional and/or alternative components as best serves a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607,843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 116 may be provided to generate power that is used to recharge the power source 125 via any suitable communication link. Additional external devices including, but not limited to, a hand held programmer (HHP) 117, a clinician programming system (CPS) 118, and/or a manufacturing and diagnostic system (MDS) 119 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump 127 may also be included within the stimulator 120. The pump 127 is configured to store and dispense one or more drugs, for example, through a catheter 123. The catheter 123 is coupled at a proximal end to the stimulator 120 and may have an infusion outlet 129 for infusing dosages of the one or more drugs at the stimulation site. In some embodiments, the stimulator 120 may include multiple catheters 123 and/or pumps 127 for storing and infusing dosages of the one or more drugs at the stimulation site.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different types, causes, or symptoms of nerve compression syndromes. Thus, in some embodiments, the stimulation parameters may be adjusted as best serves the particular patient being treated.

For example, the stimulation parameters may be adjusted so that the stimulator 120 applies a relatively low amplitude DC current to one or more stimulation sites in order to treat a particular nerve compression disorder. It is believed that low amplitude DC current is effective in helping compressed or otherwise damaged nerve axons to regenerate. The DC current may also be effective in masking pain caused by the nerve compression disorder. The low amplitude stimulation current may have an amplitude that is less than 1 milliamp (mA), for example. However, it will be recognized that the amplitude of the DC current may have any value as best serves a particular application.

In some alternative examples, the stimulation parameters may be adjusted so that the stimulator 120 applies one or more biphasic stimulation current pulses to one or more stimulation sites in order to treat a particular nerve compression disorder. An exemplary biphasic pulse includes two parts—a negative first phase having an area A1 and a positive second phase having an area A2. In some examples, the biphasic pulse is "charge balanced" because the negative area Al is equal to the positive area A2. A charge-balanced biphasic pulse is often employed as the stimulus to minimize electrode corrosion and charge build-up which can harm surrounding tissue. However, it will be recognized that the biphasic pulse may alternatively be charge-imbalanced as best serves a particular application.

In some examples, one or more stimulation pulses may be applied by an implantable stimulator 120 to a nerve to treat a nerve compression disorder by assisting in the generation or propagation of one or more action potentials. To illustrate, a brief overview of action potentials will now be given.

An electrical voltage, or potential difference, always exists between the inside and outside of a normal nerve cell. This voltage results from the distribution of ions across the cell membrane and from the permeability of the membrane to these ions. The voltage of an inactive cell stays at a negative value (inside relative to outside the cell) and varies little. When the membrane of an excitable cell is depolarized beyond a threshold, the cell will undergo (or "fire") an action potential, often called a "spike."

Hence, an action potential is a rapid swing in the polarity of the voltage from negative to positive and back. The entire cycle may only last a few milliseconds. Action potentials can propagate or travel for long distances along a nerve axon and are used to carry signals between various parts of the body and the spinal cord. This propagation is dependent on each successive segment of the nerve axon having the capacity to "fire" and regenerate the depolarization that creates the action potential.

However, if the nerve is compressed in a certain region, the myelin layer that surrounds the axons of the nerve in that region may be damaged or absent. Hence, the ability of the nerve cells to sufficiently depolarize in that region and propagate action potentials may be partially or completely impeded. The inability to effectively generate action potentials in a compressed region hampers or completely prevents propagation of signals therethrough.

For example, in a patient with carpal tunnel syndrome, the median nerve is compressed in the carpal tunnel. Hence, the ability of the median nerve cells to sufficiently depolarize and generate action potentials within the carpal tunnel may be partially or completely impeded. The inability to effectively generate action potentials in the carpal tunnel may partially or completely prevent signals from propagating from the fingers to the spinal cord.

Hence, a nerve compression syndrome may be treated by applying one or more stimulation pulses to one or more compressed nerve regions to assist in the generation or propagation of one or more action potentials therein. As used herein, the term "compressed nerve region" will refer to any region or portion of a nerve that is at least partially compressed. It will be recognized that the stimulation current may additionally or alternatively be applied to any other portion of a compressed nerve including, but not limited to, a location distal to the compressed nerve region and a location proximal to the compressed nerve region. Exemplary stimulation pulses that may be applied to compressed nerve regions to assist in the generation or propagation of one or more action potentials are described in more detail in a commonly-assigned patent application entitled "Enhancement of Neural Signal Transmission Through Damaged Neural Tissue via Hyperpolarizing Electrical Stimulation Current" to Moffitt et al. (Ser. No. 11/864,494), which application is being filed on the same day as the present application, and which application is incorporated herein by reference in its entirety.

In some examples, the stimulation parameters may also be adjusted such that the electrical and/or drug stimulation is applied to a stimulation site either intermittently or continuously. Intermittent stimulation may be more effective than continuous stimulation in some instances and vice versa.

It will be recognized that different stimuli may be applied to different stimulation sites to determine which configuration will most effectively treat a particular nerve compression syndrome for a particular patient. Moreover, the stimulation parameters may be adjusted by the patient, a clinician, or other user of the stimulator 120 as best serves the particular patient being treated. The stimulation parameters may additionally or alternatively be automatically adjusted by the stimulator 120 in response to a sensed condition, as will be described below.

The stimulator 120 of FIG. 2 is illustrative of many types of stimulators that may be used in accordance with the systems and methods described herein. For example, the stimulator 120 may include an implantable pulse generator (IPG), a spinal cord stimulator (SCS), a deep brain stimulator, a drug pump, or any other type of implantable device configured to deliver a stimulus to a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

In some examples, the stimulator 120 may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

The stimulator 120 of FIG. 2 may alternatively include a microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
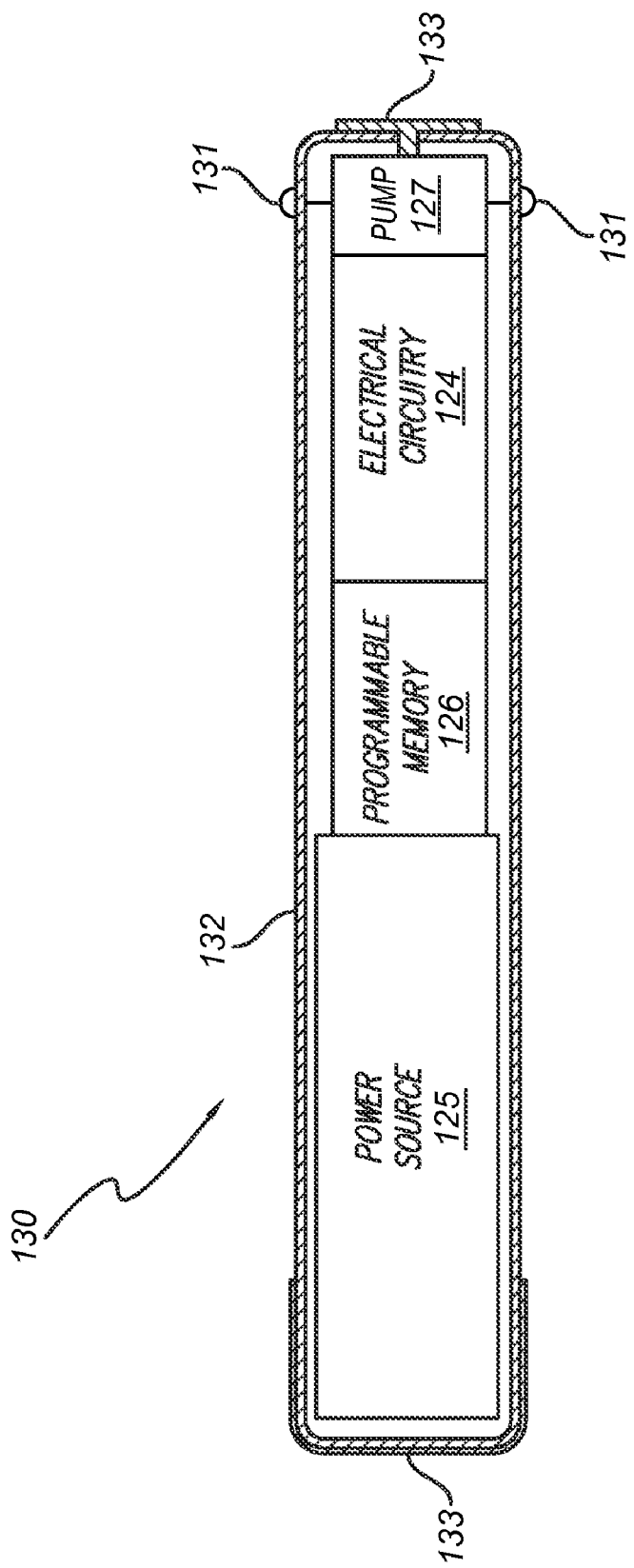
FIG. 3 illustrates an exemplary microstimulator that may be used as the stimulator according to principles described herein.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, and the pump 127 described in connection with FIG. 2. These components are housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface thereof.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4A:
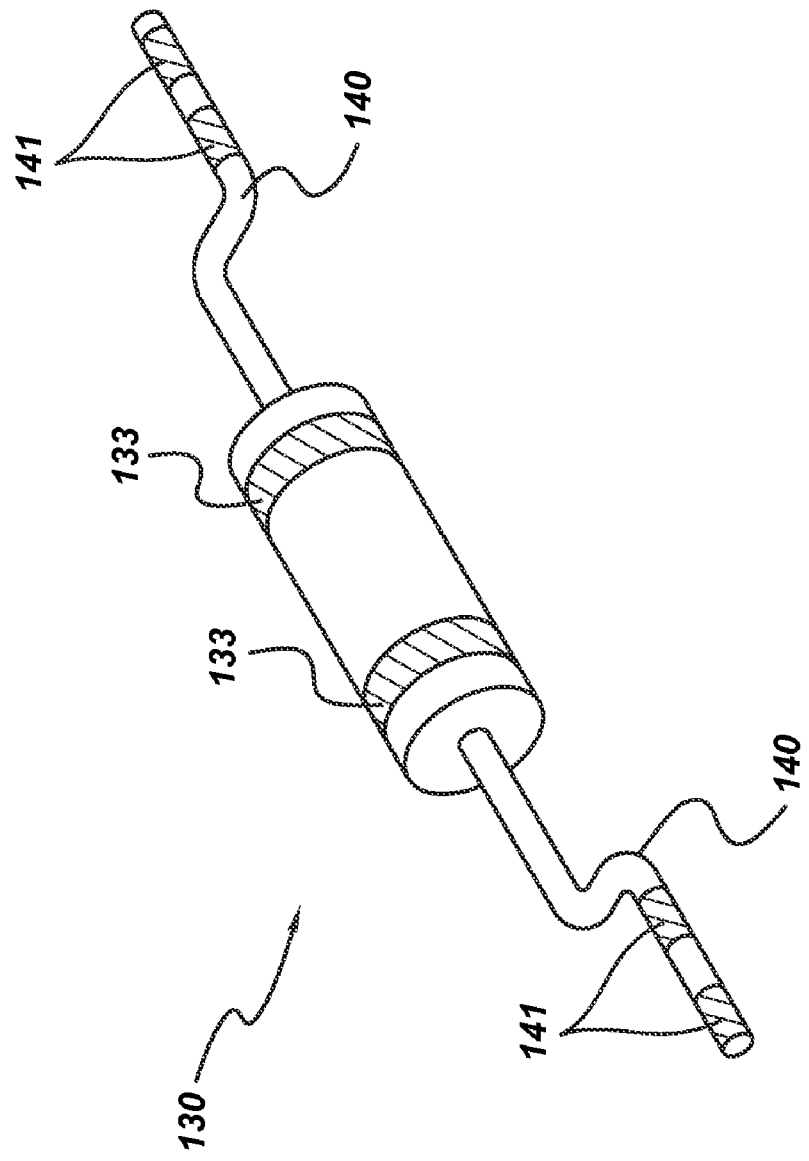
FIG. 4A shows an example of a microstimulator with one or more leads coupled thereto according to principles described herein.
Figure 4B:
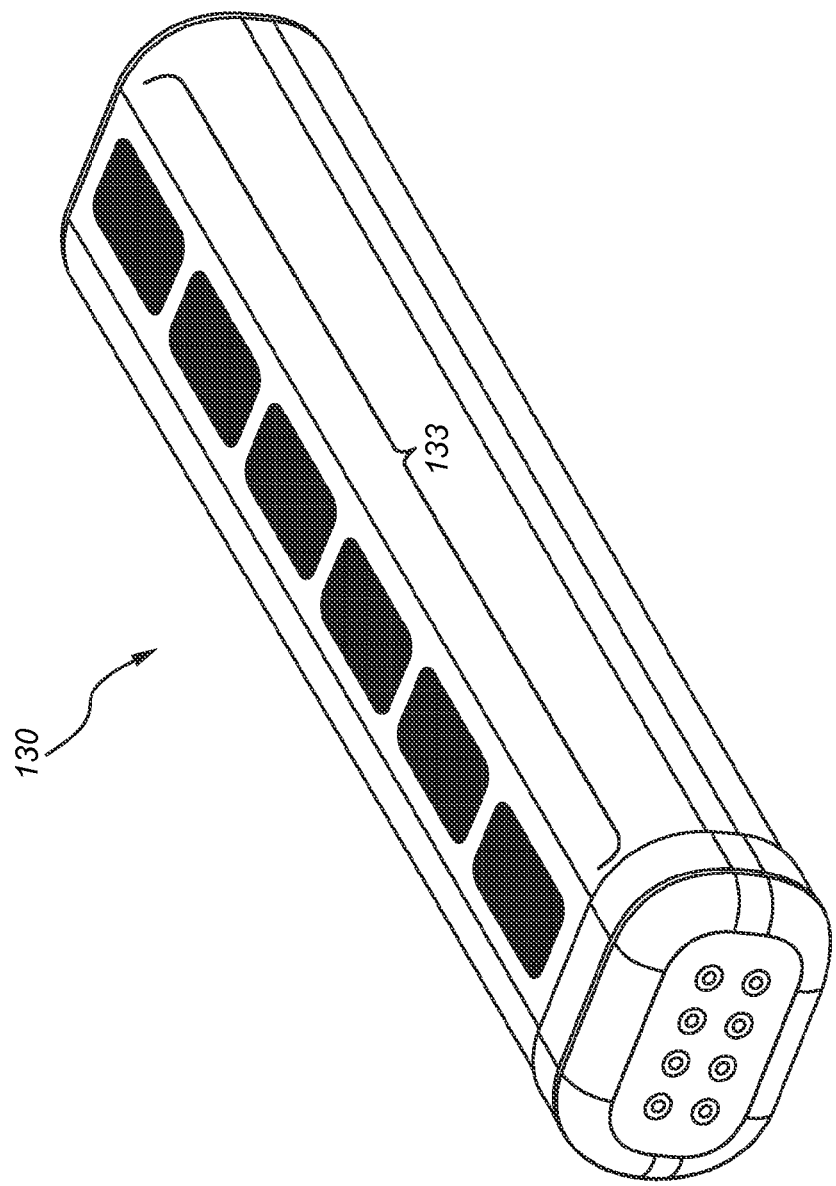
FIG. 4B shows an example of a microstimulator with a plurality of electrodes disposed on an outer surface thereof according to principles described herein.
Figure 4C:
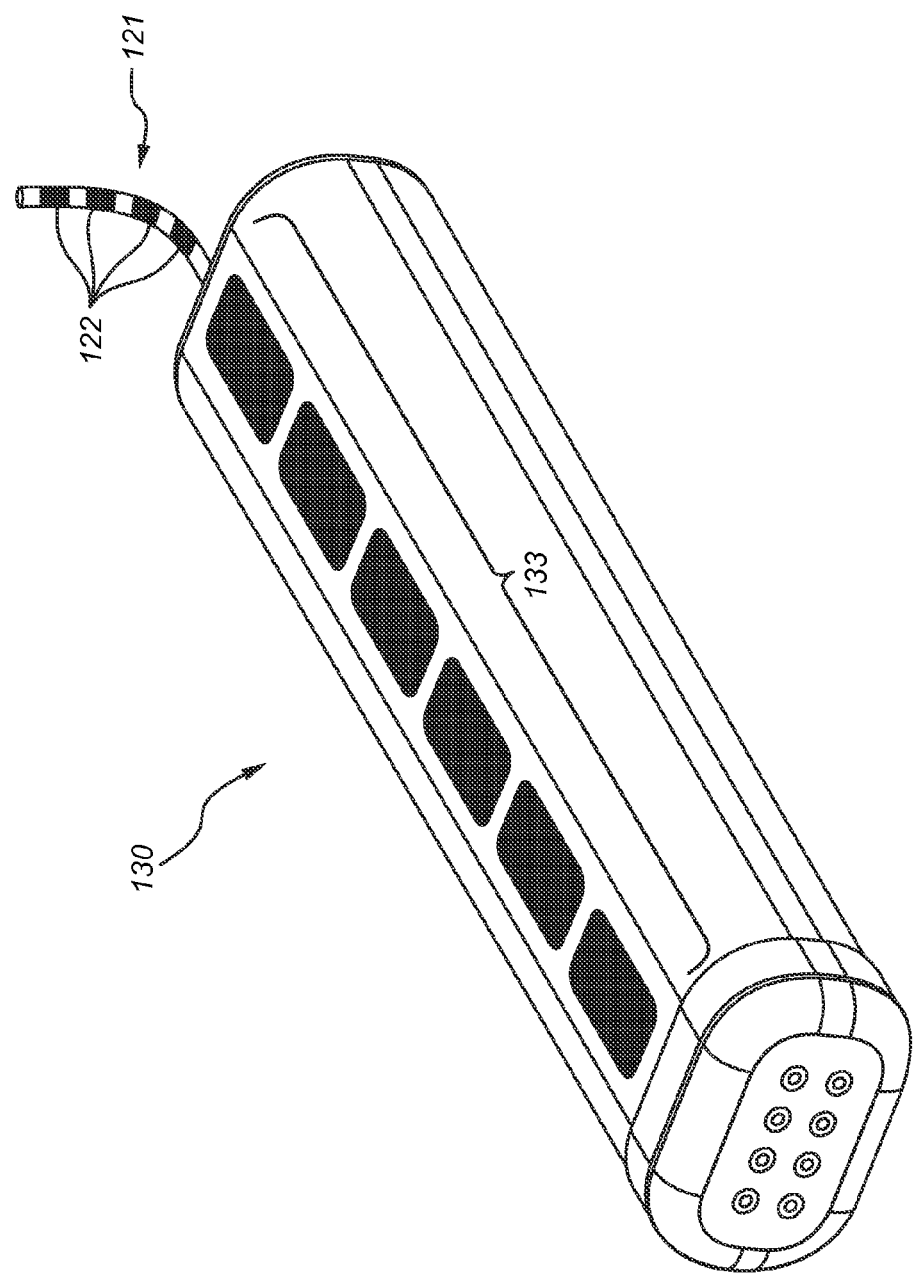
FIG. 4C shows the exemplary microstimulator of FIG. 4B coupled to a lead having a number of electrodes disposed thereon.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 133 disposed on the outer surface thereof.

FIG. 4B illustrates an exemplary microstimulator 130 with a plurality of electrodes 133 disposed on an outer surface thereof. In some examples, any number of electrodes 133 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 133 and 122 may be selectively configured to serve as an anode or as a cathode.

Figure 5:
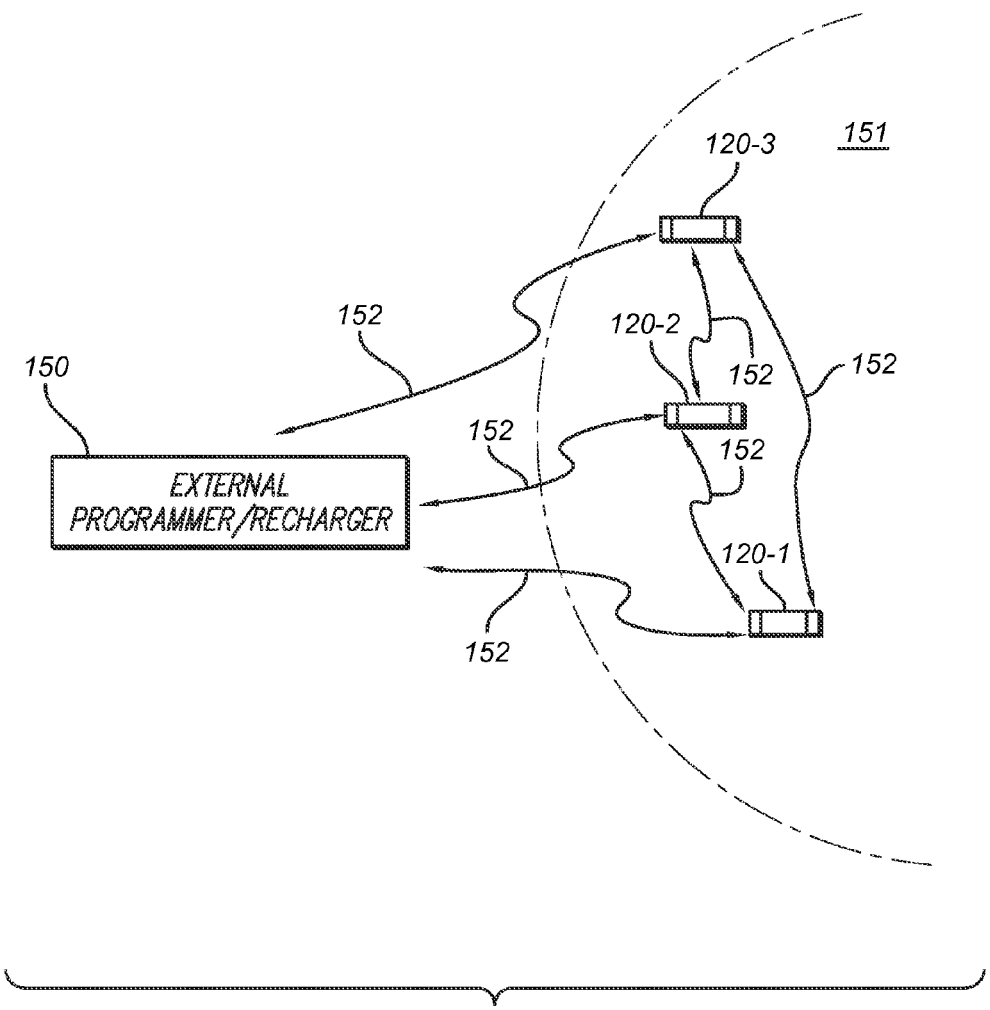
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of the symptoms or causes of a particular nerve compression syndrome and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of the nerve compression syndrome, communicate or receive data regarding such indicators, and adjust stimulation parameters accordingly.

In order to determine the strength and/or duration of electrical stimulation and/or amount and/or type(s) of stimulating drug(s) required to effectively treat a particular nerve compression syndrome, various indicators of the nerve compression syndrome and/or a patient's response to treatment may be sensed or measured. To this end, the stimulator may also include a sensor device configured to sense any of a number of indicators related to the nerve compression syndrome. For example, the stimulator 120 may include and/or be in communication with a pressure sensor or any other device configured to sense pressure exerted on a nerve or within a canal or tunnel.

In some examples, the sensor device may be disposed on the lead 121. The sensor device may alternatively be included within a separate implanted or external device configured to measure one or more indicators of the nerve compression syndrome and communicate the sensed measurements to the stimulator 120.

The indicators that may be sensed include, but are not limited to, pressure on a nerve or within a tunnel or canal, inflammation indicators, substance P levels, one or more indicators of mechanical weakness, one or more indicators of muscle tone (e.g., mechanical strain, pressure, or electromyography (EMG)), neurotransmitter levels, hormone levels, blood flow rate, medication levels within a patient, patient input (e.g., when a patient feels pain associated with a nerve compression syndrome, the patient can push a button on a remote control or other external unit to initiate stimulation), temperature of tissue in the stimulation target region, and one or more indicators of collateral tissue stimulation. In some examples, the stimulator 120 may be configured to adjust the stimulation parameters in a closed loop manner in response to one or more of these measurements.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

By way of example, an exemplary method of treating a nerve compression syndrome may be carried out according to the following sequence of procedures. The steps listed below may be modified, reordered, and/or added to as best serves a particular application.

1. A stimulator 120 is implanted so that its electrodes 122 and/or infusion outlet 129 are in communication with a stimulation site (e.g., a nerve associated with the nerve compression syndrome). As used herein and in the appended claims, the term "in communication with" refers to the stimulator 120, stimulating electrodes 122, and/or infusion outlet 129 being adjacent to, in the general vicinity of, in close proximity to, directly next to, or directly on the stimulation site.

2. The stimulator 120 is programmed to apply at least one stimulus to the stimulation site. The stimulus may include electrical stimulation, drug stimulation, gene infusion, chemical stimulation, thermal stimulation, electromagnetic stimulation, mechanical stimulation, and/or any other suitable stimulation.

3. When the patient desires to invoke stimulation, the patient sends a command to the stimulator 120 (e.g., via a remote control) such that the stimulator 120 delivers the prescribed stimulation to the stimulation site. The stimulator 120 may be alternatively or additionally configured to continuously apply the stimulation to the stimulation site and/or automatically apply the stimulation in response to sensed indicators of the nerve compression syndrome.

4. To cease stimulation, the patient may turn off the stimulator 120 (e.g., via a remote control).

5. Periodically, the power source 125 of the stimulator 120 is recharged, if necessary, in accordance with Function 1 described above.

In other examples, the treatment administered by the stimulator 120, i.e., drug therapy and/or electrical stimulation, may be automatic and not controlled or invoked by the patient. It will be recognized that the particular stimulation methods and parameters may vary as best serves a particular application.

The stimulator 120 may be implanted within a patient using any suitable surgical procedure such as, but not limited to, small incision, open placement, laparoscopy, or endoscopy. Exemplary methods of implanting a microstimulator, for example, are described in U.S. Pat. Nos. 7,193,539; 5,193,540; 5,312,439; 6,185,452; 6,164,284; 6,208,894; and 6,051,017. Exemplary methods of implanting an SCS, for example, are described in U.S. Pat. Nos. 7,501,703; 6,487,446; and 6,516,227. Exemplary methods of implanting a deep brain stimulator, for example, are described in U.S. Pat. Nos. 7,938,688; 6,016,449; and 6,539,263. All of these listed patents are incorporated herein by reference in their respective entireties.

Figure 6:
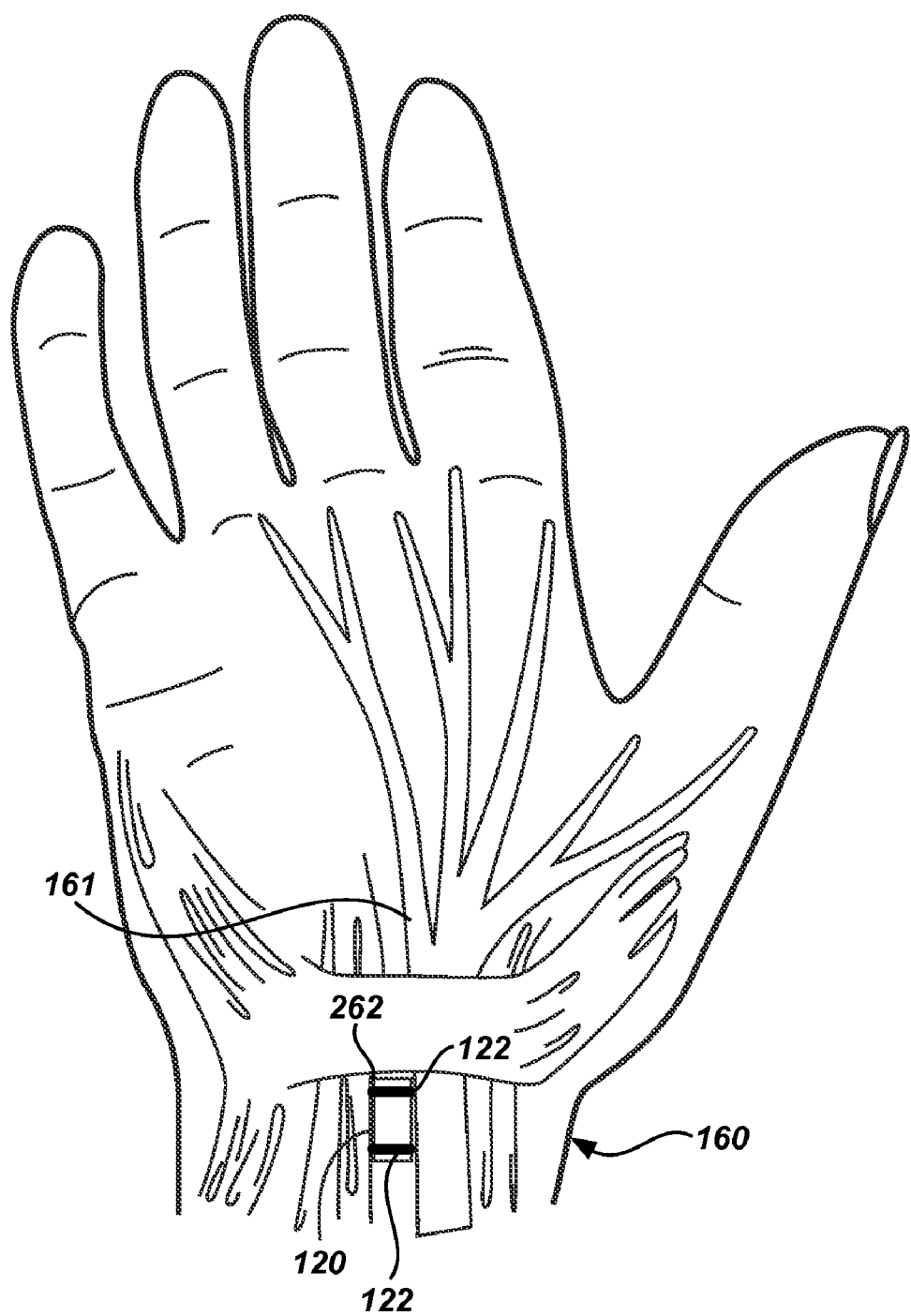
FIG. 6 shows a stimulator implanted within the wrist such that stimulation may be applied to a portion of the median nerve that passes through the carpal tunnel according to principles described herein.

To illustrate, the stimulator 120 and/or electrodes 122 may be implanted such the electrodes 122 are in communication with a compressed nerve region. For example, FIG. 6 shows a stimulator 120 implanted within the wrist 160 such that stimulation may be applied to a portion of the median nerve 161 that passes through the carpal tunnel 162. As shown in FIG. 6, the stimulator 120 is leadless and includes a number of electrodes 122 disposed on its surface. In this manner, stimulation may be applied to the median nerve 161 via the electrodes 122 in order to treat carpal tunnel syndrome. It will be recognized that a lead with a number of electrodes 122 disposed thereon may additionally or alternatively be coupled to the stimulator and implanted such that the electrodes 122 are in communication with the carpal tunnel 162.

In some examples, the stimulator 120 may be implanted as shown in FIG. 6 at the end of a surgery to alleviate pressure from a compressed nerve region. For example, the stimulator 120 may be implanted at the end of a surgery to release the ligaments overlying the carpel tunnel.

Figure 7:
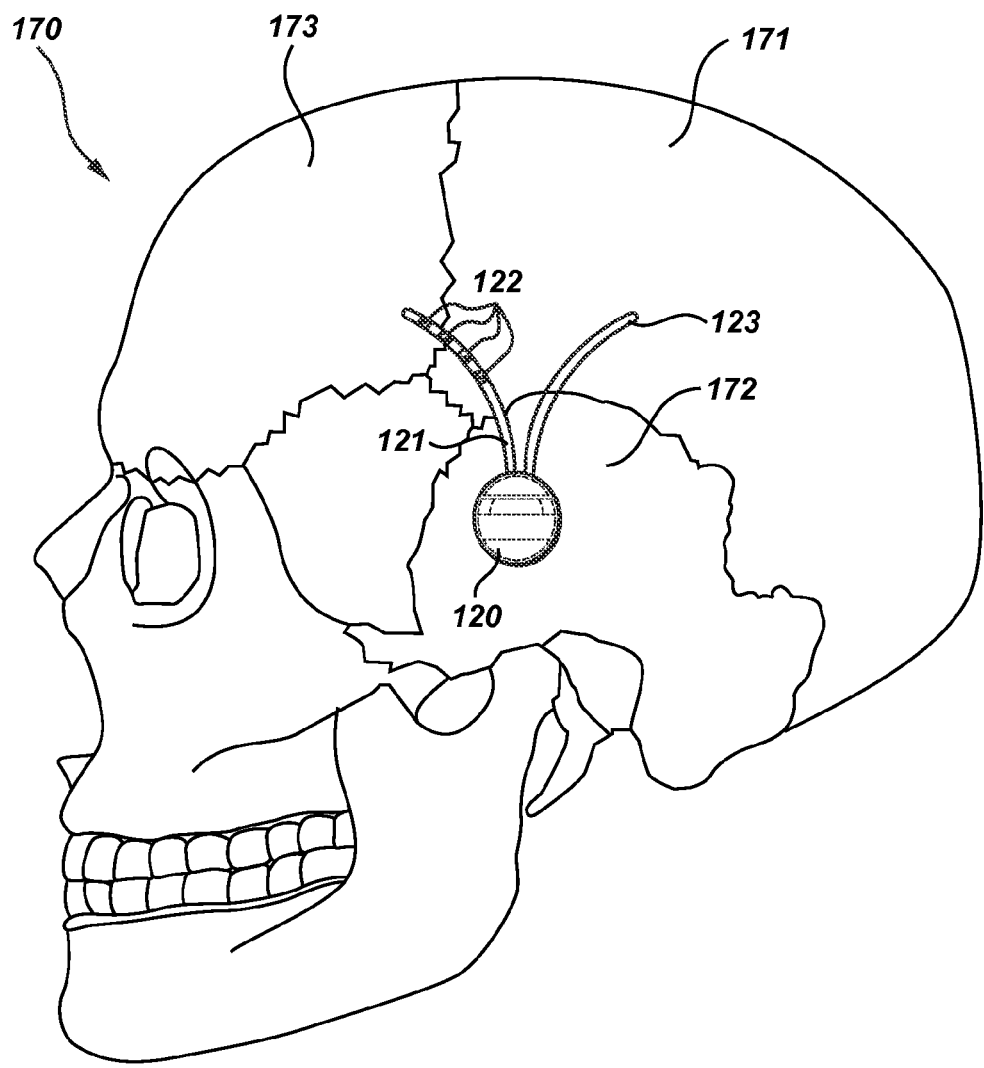
FIG. 7 illustrates a stimulator that has been implanted beneath the scalp of a patient to stimulate a stimulation site within the brain according to principles described herein.

In some alternative examples, the stimulator 120 may be implanted beneath the scalp of a patient to stimulate a stimulation site within the brain (e.g., one or more of the cranial nerves). For example, as shown in FIG. 7, the stimulator 120 may be implanted in a surgically-created shallow depression or opening in the skull 170. The depression may be made in the parietal bone 171, temporal bone 172, frontal bone 173, or any other bone within the skull 170 as best serves a particular application. The stimulator 120 may conform to the profile of surrounding tissue(s) and/or bone(s), thereby minimizing the pressure applied to the skin or scalp. Additionally or alternatively, the stimulator 120 may be implanted in a subdural space over any of the lobes of the brain, in a sinus cavity, or in an intracerebral ventricle.

In some embodiments, as shown in FIG. 7, a lead 121 and/or catheter 123 s run subcutaneously to an opening in the skull 170 and passes through the opening such that it is in communication with a stimulation site in the brain. Alternatively, the stimulator 120 is leadless and is configured to generate a stimulus that passes through the skull. In this manner, a stimulation site within the brain may be stimulated without having to physically invade the brain itself.

It will be recognized that the implant locations of the stimulator 120 illustrated in FIGS. 6-7 are merely illustrative and that the stimulator 120 may additionally or alternatively be implanted in any other suitable location within the body.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   implanting a stimulator within a patient such that the stimulator is in communication with a stimulation site, wherein said stimulation site comprises at least one of a compressed region of a nerve associated with a nerve compression syndrome, a location along said nerve associated with said nerve compression syndrome that is distal to said compressed region, and a location along said nerve associated with said nerve compression syndrome that is proximal to said compressed region;
   programming said stimulator with one or more stimulation parameters configured to treat said nerve compression syndrome; and
   applying at least one stimulus with said stimulator to a stimulation site within said patient in accordance with said one or more stimulation parameters;
   wherein said at least one stimulus is configured to treat a nerve compression syndrome.

2. The method of claim 1, wherein said stimulator is coupled to one or more electrodes, and wherein said stimulus comprises a stimulation current delivered via said electrodes.

3. The method of claim 2, wherein said stimulator is leadless and wherein electrodes are disposed on an outer surface of said stimulator.

4. The method of claim 2, wherein said stimulation current is configured to assist in at least one of a generation and a propagation of one or more action potentials.

5. The method of claim 2, wherein said stimulation current comprises a DC current.

6. The method of claim 1, further comprising sensing at least one indicator related to said nerve compression syndrome and using said at least one sensed indicator to adjust one or more of said stimulation parameters.

7. The method of claim 1, wherein said stimulus is configured to mask pain associated with said nerve compression syndrome.

8. The method of claim 1, wherein said stimulus comprises one or more drugs delivered to said stimulation site.

9. The method of claim 1, wherein the nerve compression syndrome is selected from the group consisting of: cubital tunnel syndrome, radial tunnel syndrome, pronator syndrome, high radial nerve palsy, lateral antebrachial cutaneous nerve entrapment syndrome, meralgia paresthetica, tarsal tunnel syndrome, compressed peroneal nerve, thoracic outlet syndrome, obturator nerve compression, lateral femoral cutaneous nerve compression, and trigeminal neuralgia.

10. The method of claim 9, wherein the nerve compression syndrome is selected from the group consisting of: high radial nerve palsy, lateral antebrachial cutaneous nerve entrapment syndrome, obturator nerve compression, lateral femoral cutaneous nerve compression, and trigeminal neuralgia.

11. The method of claim 1, wherein the stimulation site is selected from the group consisting of: the lateral femoral cutaneous nerve, the suprascapular nerve, the anterior interosseous nerve, the lateral antebrachial cutaneous nerve, the brachial plexus, the obturator nerve, the peroneal nerve, the sciatic nerve, the tibial nerve, and a cranial nerve.

12. The method of claim 11, wherein the stimulation site is selected from the group consisting of: the lateral antebrachial cutaneous nerve, the obturator nerve, the lateral femoral cutaneous nerve, and a cranial nerve.

13. A method of treating a nerve compression syndrome, said method comprising:
   implanting a stimulator within a patient such that the stimulator is in communication with a stimulation site wherein said stimulation site comprises at least one of a compressed region of a nerve associated with a nerve compression syndrome, a location along said nerve associated with said nerve compression syndrome that is distal to said compressed region, and a location along said nerve associated with said nerve compression syndrome that is proximal to said compressed region;
   programming said stimulator with one or more stimulation parameters; and
   applying a stimulation current with said implanted stimulator to a compressed nerve region within said patient in accordance with said one or more stimulation parameters;
   wherein said one or more stimulation parameters and resulting stimulation current are configured to treat said nerve compression syndrome by assisting one or more nerve cells in said compressed nerve region to generate one or more action potentials.

14. The method of claim 13, wherein said one or more action potentials are configured to propagate a signal through said compressed nerve region.

15. The method of claim 13, wherein said stimulation current comprises a DC current.

16. The method of claim 13, wherein one or more electrodes are disposed on an outer surface of said stimulator and wherein said stimulation current is applied to said compressed nerve region via said one or more electrodes.

17. The method of claim 13, wherein said nerve compression syndrome comprises carpal tunnel syndrome.

18. The method of claim 13, further comprising sensing at least one indicator related to said nerve compression syndrome and using said at least one sensed indicator to adjust one or more of said stimulation parameters.

19. A system for treating a nerve compression syndrome, said system comprising:

a stimulator configured to be implanted at least partially within a patient, in communication with a stimulation site, wherein said stimulation site comprises at least one of a compressed region of a nerve associated with said nerve compression syndrome, a location along said nerve associated with said nerve compression syndrome that is distal to said compressed region, and a location along said nerve associated with said nerve compression syndrome that is proximal to said compressed region, and to generate at least one stimulus in accordance with one or more stimulation parameters adjusted to treat said nerve compression syndrome;

a programmable memory unit in communication with said stimulator and programmed to store said one or more stimulation parameters to at least partially define said stimulus such that said stimulus is configured to treat said nerve compression syndrome; and means, operably connected to said stimulator, for applying said stimulus to a stimulation site within said patient.

20. The system of claim 19, wherein said means for applying said at least one stimulus comprises one or more electrodes, and wherein said stimulus comprises a stimulation current delivered via said electrodes.

* * * * *